United States Patent [19]

Barrandon et al.

[11] Patent Number: 4,888,291

[45] Date of Patent: Dec. 19, 1989

[54] HUMAN EPITHELIUM ORIGINATING FROM CELL CULTURES

[75] Inventors: Yann Barrandon, Boston; Howard Green, Brookline, both of Mass.

[73] Assignee: President and Fellows of Harvard College, Cambridge, Mass.

[21] Appl. No.: 64,046

[22] Filed: Jun. 19, 1987

[51] Int. Cl.$^4$ ............................................. C12N 5/00
[52] U.S. Cl. ........................ 435/240.241; 435/240.23; 435/240.243
[58] Field of Search ..................... 435/240.23, 240.243, 435/240.241

[56] References Cited

U.S. PATENT DOCUMENTS

| | | | |
|---|---|---|---|
| 4,254,226 | 3/1981 | Eisinger et al. | 435/240.23 |
| 4,304,866 | 12/1981 | Green et al. | 435/240.23 |
| 4,673,649 | 6/1987 | Boyce et al. | 435/240.25 |

OTHER PUBLICATIONS

Banks-Schlegel and Green, 29 Transplantation 308, 1980.
Worst et al., 53 J. Nat. Can. Inst. 1061, 1974.
Karasek, 51 J. Invest. Derm. 247, 1968.

*Primary Examiner*—John E. Tarcza

[57] ABSTRACT

Generating a human epithelium on a living animal by a method in which cultured human keratinocytes are placed in contact with the subdermal connective tissue of a non-human animal.

12 Claims, 4 Drawing Sheets

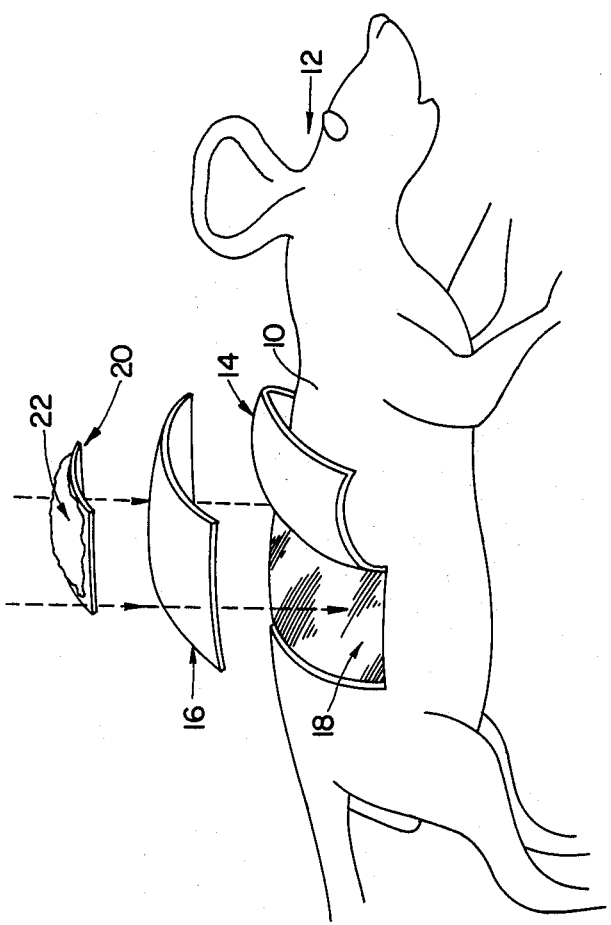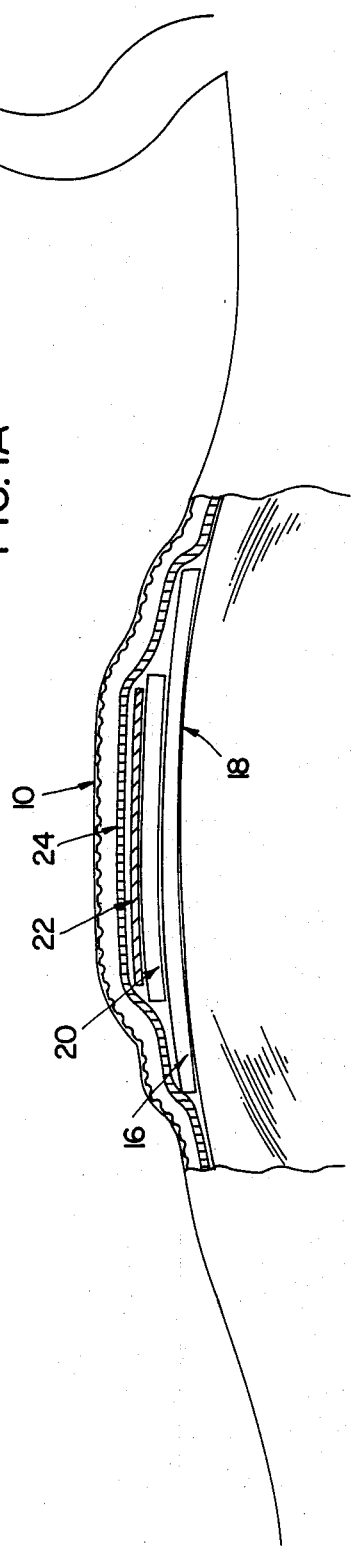

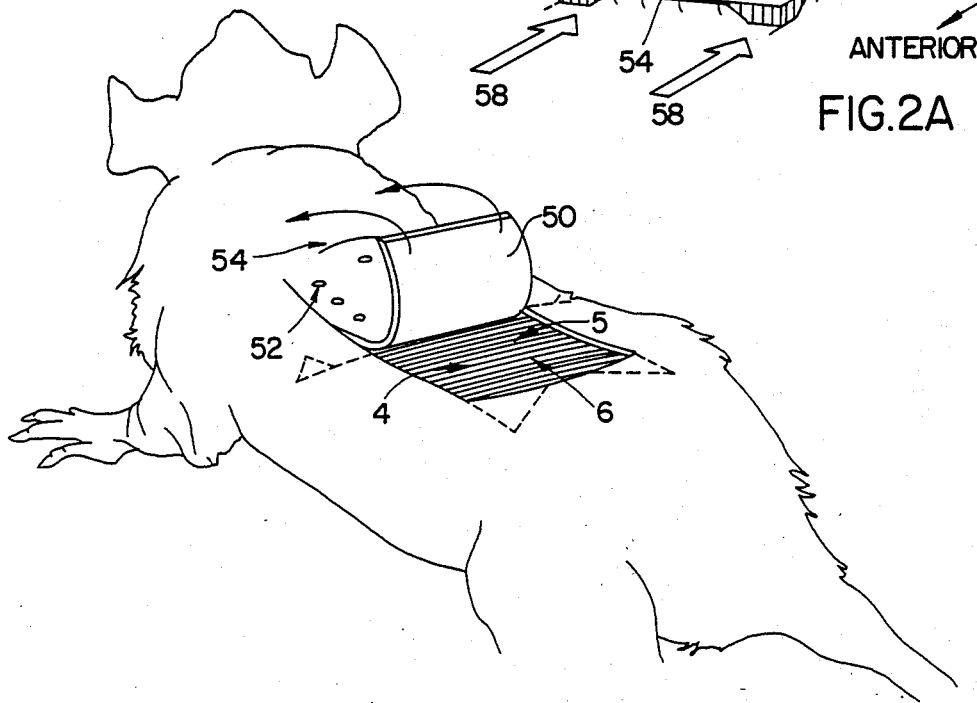
FIG.2
FIG.2A
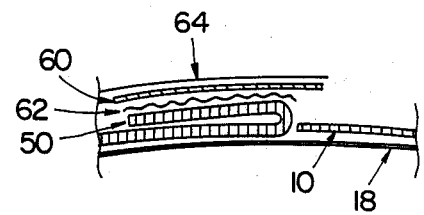
FIG. 2C
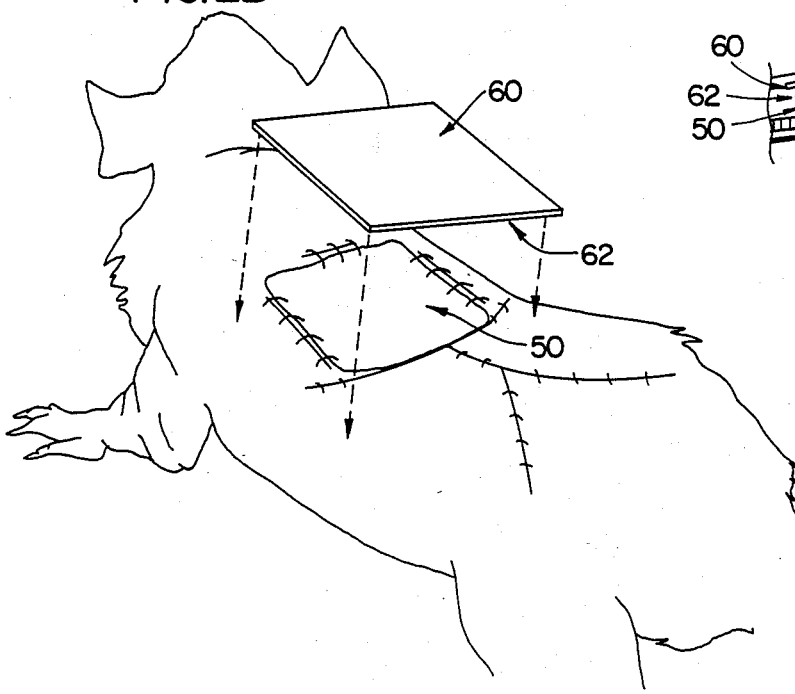
FIG.2B

HUMAN EPITHELIUM ORIGINATING FROM CELL CULTURES

BACKGROUND OF THE INVENTION

This invention relates to generating epidermis or other coherent epithelia from cultured human cells.

Banks-Schlegel and Green, 29 *Transplantation* 308, 1980, describe growing human epidermal cells in surface culture by inoculation into medium suspensions of disaggregated cells. These cells grow into colonies and the colonies fuse to form a confluent epithelium which can be detached and transplanted to athymic mice. Specifically, full-thickness skin was removed from athymic animals and the graft was applied to the fascia covering the thoracic wall. Such grafts form epidermis having all cell layers, including a stratum corneum. "Although they become considerably reduced in area, the grafts remain healthy for as long as 108 days after grafting." Id. at 308. However, after 10 days from grafting "no information could be obtained by inspection of the graft because the human epidermis could not be distinguished with certainty from that of the mouse . . . " Id. at 312. Human epidermis was identified using species-specific antiserum and examination of microscopic sections.

Worst et al., 53 *J. Nat. Can. Inst.* 1061, 1974 and Karasek, 51 J. Invest. Derm. 247, 1968, describe the use of glass or silicone chambers for growing epidermis from implanted epidermal cell cultures. The chambers are inserted under the wound edge after the epidermis and dermis are excised down to the muscle fascia. Such chambers prevent wound contraction but "intense hyperplasia was common in every transplantation site." (Id. at 251. Further, there was "a complete deterioration of the transplanted cells within 6 weeks . . ." Such deterioration may be ". . . a direct consequence of a change in the normal connective tissue environment . . ." Id. at 251. Karasek suggested that such explant cultures "can provide an experimental approach to a study of the factors that affect somatic stability of epithelial cells in cell culture." Id. at 251.

Krueger et al. 5 *Fundamental and Applied Toxicology* S112, 1985, describe a process of skin grafting in four stages. In the first stage a skin graft is placed inside an epigastric flap of a rat. In later stages, the femoral vessels supplying this graft are isolated, the flap removed through a subdermal tunnel to the dorsal side of the rat, and stitched in place.

SUMMARY OF THE INVENTION

We have discovered a method of generating an epithelium from cultured keratinocytes, by contacting the keratinocytes with the subdermal connective tissue of a living non-human animal. The term keratinocytes includes not only those cells which form epidermis, but also those which form the wet surfaced squamous epithelia mentioned below.

Preferably, disaggregated keratinocytes are first cultured to form a confluent culture which is then contacted with the animal's subdermal connective tissue. For example, epidermal cells are grown to form an epithelium which is detached from the vessel surface and placed in contact with that connective tissue. Alternately, the cells could be grown to subconfluence on a plastic membrane and applied directly to the graft bed, while still attached to the membrane. In either case, the graft is applied to the inner surface of the flap, consisting of subdermal connective tissue containing the panniculus carnosus.

One method of contacting the keratinocytes with the animal tissue comprises incising a flap of skin of the animal and placing the confluent culture (e.g. an epithelial sheet) beneath the flap, which is then sutured in its original position. In a second method, the confluent culture or epithelial sheet is applied in the same way, the cells are allowed to form a human epidermis, and the flap is then everted to expose its inner surface bearing the epidermis. In a third method, the flap of skin is everted and fastened to the animal before placing the confluent culture or epithelial sheet in position. The epithelial sheet used as a graft may be grown in culture from epidermal cells and may be placed on a plastic membrane in order to conveniently apply it to the graft bed.

This invention provides methods for generating typical human epidermis within 7 days from cultured human epidermal cells grafted onto a living animal. The resulting epidermis undergoes relatively little contraction, and it is readily apparent which layer is human epidermis and which is the epidermis of the recipient animal. The epidermis created is also histologically normal.

The above method provides sufficient human epidermis for investigative and toxicological studies. For example, it is possible to test chemicals, such as cosmetics, on human epidermis, or on human wet surfaced squamous epithelia composed of other kinds of keratinocytes—corneal, conjunctival, oral, esophageal and vaginal—all of which can be grown by the same technique as described for epidermal cells. Other studies include transepidermal absorption of specific chemicals, and the effect of aging and the expression of mutations on epidermal function. Finally, it is possible to study the expression in human epidermis of exogenous genes previously introduced into the cells.

Other features and advantages of the invention will be apparent from the following decription of the preferred embodiments thereof and from the claims.

DESCRIPTION OF THE PREFERRED EMBODIMENTS

The Figures will first briefly be described.

DRAWINGS

FIGS. 1 and 2 are diagrammatic representations of grafting techniques;

METHODS

Figure 3:
FIG. 3 is a section through mouse epidermis and a human epidermal graft.

In general, the preferred grafting method of the invention involves placing cultured human epithelium with the basal cell layer in contact with the subdermal connective tissue on the underside of a host animal's skin. This connective tissue layer is exposed at the internal surface of a skin flap elevated at the most easily cleaved layer; in rodents this connective tissue contains the panniculus carnosus. The layers present in the flap thus include the epidermis, dermis and subdermal connective tissue (including panniculus carnosus, contrary to what is stated in Banks-Schlegel and Green cited above). The layer exposed on the trunk of the animal is thoracic wall muscle.

Once the epithelium is applied to the subdermal connective tissue, the flap is replaced either in its original position or in a new position. Two examples of such methods are given below; these examples are not meant to be limiting to the invention; those skilled in the art will realize that many equivalent techniques can be devised and are included in the invention.

In the example described below, all animals were obtained from Taconic Farm (New York). Male or female mice were of strains NIH Swiss nu/nu or C57 Bl/6 nu/nu, and were at least 8-10 weeks old (or 19-20 g body weight). Rats were of strain Tac:N:NIH-rnu and were at least 5 weeks old or 120 g body weight. Mice were anesthetized by a subdermal injection of sodium pentobarbital (0.038 mg/g body weight, Anthony Products Co., Arcadia Ca.) and Xylazine 0.075 mg/g body weight (Hauer-Lockhart, Kansas) according to Worst et al. (53 *J. Nat. Cancer Res.* 1061, 1974). Rats were anesthetized with a similar mixture but at one tenth the dose.

After completion of surgery, animals were allowed to recover in a warm atmosphere (30° C.), and caged separately. As alternatives to nude mice, animals whose immune system is suppressed, for example, by chemicals such as cyclosporin, are also suitable for the methods described below. It is only necessary that the animal not reject the human graft by an immune response.

Cell Culture

Human epidermal cells were obtained from foreskins of newborns and were cultivated on lethally irradiated feeders of 3T3 -J2 cells (Rheinwald et al., 6 Cell 331, 1975). Cell inocula varied from $2\times10^4$ to $2\times10^5$ cells depending on the size of the culture vessel. Cultures were fed every 3-4 days and were usually confluent within a week. The composition of the medium has been described by Simon and Green 40 Cell 677, 1985. Other cell strains derived from any stratified squamous epithelium (corneal, conjunctival, oral and esophageal, and vaginal) from donors of any age can be used in the methods of the invention. Strains or lines having known mutations or growth alterations can be grown to study the effect of these changes on the resulting epidermis.

Preparation of Grafts

A confluent culture was washed with serum-free medium and detached intact from the surface of the culture dish by incubation with solution of Dispase II (Boehringer Mannheim, Indianapolis, Indiana) as described by Green et al., 76 *Proc. Natl. Acad. Sci.*, USA 5665 (1979). The original polarity of the culture was maintained (basal cell layer facing the bottom of the dish). The detached epithelial sheet was washed twice with serum-free medium which was then completely removed. Rectangular sheets of silicone rubber were prepared in advance by washing according to the manufacturer's recommendations (Silastic ®, Dow Corning, N.J., 0.005 or 0.01 mm thickness). A sterile sheet of Silastic ® #1, slightly larger than the epithelial sheet was gently deposited over it and trapped air bubbles were expressed. The graft was kept moist and exposed to 10% $CO_2$ at 37° C. until it was applied. Equivalent, inert plastic sheets composed of other materials can also be used.

Grafting

All surgical procedures were carried out on anesthetized animals, under sterile conditions using a laminar flow hood.

EXAMPLE 1

Referring to FIG. 1, the dorsal skin 10 of the animal 12 was disinfected with alcohol and a rectangular flap 14 was incised with scissors and lifted. Special care was taken not to damage the well vascularized inner surface of the flap. A sheet of Silastic ® #2 (16), slightly larger than the flap, was inserted over the thoracic wall 18. With the help of forceps, Silastic ® #1 (20), with its adhering epithelial sheet 22, was carefully lifted from the culture dish and deposited over Silastic ® #2 with the basal surface of the epithelium facing upwards. The epithelium was spread out with a rubber policeman and flap 14, which had been kept moist with a drop of medium, was folded back in place over the graft (FIG. 1a), such that the connective tissue 24 was on contact with the epithelium. The incision was then closed with either sutures or surgical clips. The entire surgical procedure usually took from 15 to 20 minutes.

To harvest the graft 1 to 2 weeks later, the animal was either anesthetized or sacrificed. A skin flap was raised as in making the graft. This flap contained the animal epidermis on it outer surface and human epidermis generated from the graft on its inner surface.

Biopsies were made and either fixed in 3.7% formaldehyde and paraffin embedded or snap frozen in liquid nitrogen. 5 μm paraffin embedded sections were stained with hematoxylin and eosin. 6μ frozen sections were stained by an immunoperoxidase technique using the IgG fraction of a rabbit serum anti-involucrin. Referring to FIG. 3, microscopic section through a graft made by the above technique shows a sandwich consisting of two epidermal coverings, the outer consisting of rodent epidermis 30, and the inner of human epidermis 32—the two separated by supporting connective tissue 34. The mouse epidermis is shown at the extreme left, followed by dermis 36, hypodermis 38, muscle 40 (panniculus carnosus), loose and dense subdermal connective tissue 34, and human epidermis 32. The human epidermis contains well-developed Malpighian and granular layers, as well as a thick cornified layer 42. The human epidermis is substantially thicker than the rodent epidermis and lacks adnexal structures such as hair follicles and sebaceous glands. Separation of the two epithelia by connective tissue prevents confusion as to the species of origin of each part; nevertheless, the human origin of the regenerated epidermis was confirmed by the presence of involucrin as revealed by immunoperoxidase, using an antiserum to the protein.

EXAMPLE 2

This technique was used mainly on the rat. Referring to FIG. 2, a skin flap 50 (2×3 cm) was raised as in Example 1, but was then everted so that half of its inner surface was exposed (FIG. 2). The everted flap was then spot-welded in position by the application of a cyanoacrylate cement 52 (Quick Gel, Locktite Corp., Cleveland, Ohio). The adjacent skin was incised, as shown by thick lines in FIG. 2a and at 54, and each edge of the flap (shown as circled numbers 1, 2 and 3, and by arrows 4, 5 and 6) was sutured with sutures 56 to the adjacent border of the incised skin (FIG. 2a); the healing of the opposed edges provided the flap with anchorage, thereby retarding contraction. The skin 54 just anterior to the everted flap 50 was incised and similarly sutured. Care was taken that this incision was long enough to provide a good anchorage, but short enough to minimize destruction of the vascularization. A 0.5 to 1 cm incision appeared to be effective (FIG. 2a). The path of vascularization of the flap is shown by arrows 58 in FIG. 2a.

Referring to FIG. 2b, a sheet of Silastic ® 60, (shown in side view in FIG. 2c) bearing the cultured epithelium 62, was then applied with the basal layer facing the vascularized surface of the flap 50. The Silastic ® was maintained in place by the application of an adhesive transparent dressing 64 (Bioclusive and Dermiclear, Johnson and Johnson, New Brunswick, NJ). The dressing was usually removed after 5–7 days and the graft was then exposed to the air.

Figure 4:
FIG. 4 is a section through a human epidermal graft.

This technique result in the formation of human epidermis, in the same location vis-a-vis the rodent epidermis as in Example 1, but exposed to air by eversion of the flap. The epidermis is similarly thick, well organized and robust (FIG. 4), shows at high magnification only the human epidermis 70 and underlying connective tissue 72).

Alternatively, in a third example, a flap could be everted sometime after grafting by the technique in Example 1. This allows the cultured epithelium to form a mature epidermis before it was exposed to the outside air. For example, 8 days after grafting, as in Example 1, the flap was exposed and the fully formed human epidermis observed over a period of two weeks or more.

Shrinkage of the graft is considerably reduced by these techniques, presumably because the subdermal connective tissue and dermis are not removed. In addition, incising and suturing the edges of the flap, as in Example 2, appear to anchor the graft bed and delay its contraction.

Applications of the Method

The grafting techniques described here can be applied to different studies on the structure and functions of human epidermis. The technique shown in Example 1 has been used for studies of gene transfer to human epidermal cells. This type of graft can also be used for studies of wet-surfaced squamous epithelia such as corneal, conjunctival, oral, esophageal and vaginal, all of which can be grown in culture by the same method as epidermal cells.

The technique shown in Example 2 is preferred for studies of human epidermis in its natural state in which the cornified layer is dehydrated. For example, studies on transepidermal absorption and toxicity can be performed on such graft. The effect of aging on epidermal function and the expression of mutations also can be studied. When a part of the recipient bed remains uncovered by human epidermis, either by making the graft small, or by subsequent removal of a portion of the epidermis, the cells multiply, migrate outward, and cover more of the exposed connective tissue. This is a model for healing of human epidermal wounds and can be used to evaluate the effect of agents thought to promote such healing. Since very small biopsies suffice for the generation of cultures, uniform material can be generated on many animals and experiments may therefore be well controlled.

Other uses include: (a) Studying the interaction of he human epidermis with toxic substances. In these studies, the time from application of a substance to onset of symptoms can be measured, and the protective effect of various creams studied. (b) Studying the capacity of human skin to metabolize compounds. (c) Studying the effect of agents on enhancement of drug delivery through the skin.

Other embodiments are within the following claims.

We claim:

1. A method of growing an epithelial sheet comprising culturing disaggregated human keratinocytes and placing said human keratinocytes in direct contact with the living subdermal connective tissue of a living non-human animal, and maintaining said connective tissue as living tissue in contact with dermis of said non-human mammal, said connective tissue being positioned between said human kertinocytes and said dermis of said non-human mammal.

2. The method of claim 1 comprising culturing disaggregated human keratinocytes to form a confluent culture and contacting said confluent culture with subdermal connective tissue of said animal.

3. The method of claim 2 wherein said confluent culture is placed on a plastic membrane prior to said contacting.

4. The method of claim 1 or claim 2 in which said human keratinocytes are placed in direct contact with living subdermal connective tissue by incising a flap of skin of said animal and positioning said cultured keratinocytes beneath said flap.

5. The method of claim 4 further comprising fastening said flap of skin to said animal after positioning said cultured keratinocytes in contact with said flap.

6. The method of claim 4 wherein, after positioning said keratinocytes beneath said flap, a mature epidermis is formed beneath the flap, and the flap and epidermis are everted.

7. The method of claim 1 or claim 2 in which said human keratinocytes are placed in direct contact with living subdermal connective tissue by: (a) incising a flap of skin of said animal; (b) everting said skin to expose the inner surface of said skin; and (c) positioning said keratinocytes in contact with said inner surface of said skin.

8. The method of claim 8 comprising fastening said flap or skin to said animal after positioning said keratinocytes in contact with said flap.

9. The method of claim 2 wherein said dissaggregated keratinocytes are epidermal cells which are grown in culture to form an epithelium prior to said contacting.

10. The method of claim 1 or claim 2 wherein said subdermal connective tissue is adjacent to the dermis of said animal.

11. The method of claim 1 or claim 2 wherein said subdermal connective tissue contains panniculus carnosus.

12. The method of claim 1 wherein disaggregated keratinocytes are grown to subconfluence on a plastic membrane and contacted with said subdermal connective tissue.

* * * * *

UNITED STATES PATENT AND TRADEMARK OFFICE
CERTIFICATE OF CORRECTION

PATENT NO. : 4,888,291

DATED : December 19, 1989

INVENTOR(S) : Barrandon et al.

It is certified that error appears in the above-identified patent and that said Letters Patent is hereby corrected as shown below:

Column 1, line 1, before "Background of the Invention" please insert the following -- This invention was made with government support under Grant Nos. GM33158 and CA40029 awarded by the National Institutes of Health. The government has certain rights in the invention. --

Signed and Sealed this

Thirteenth Day of October, 1992

*Attest:*

DOUGLAS B. COMER

*Attesting Officer*     *Acting Commissioner of Patents and Trademarks*